US012045985B2

(12) United States Patent
Nishide

(10) Patent No.: US 12,045,985 B2
(45) Date of Patent: Jul. 23, 2024

(54) PROGRAM, INFORMATION PROCESSING METHOD, AND INFORMATION PROCESSING DEVICE

(71) Applicant: HOYA CORPORATION, Tokyo (JP)

(72) Inventor: Akihiko Nishide, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 396 days.

(21) Appl. No.: 17/615,979

(22) PCT Filed: Oct. 26, 2020

(86) PCT No.: PCT/JP2020/040092
§ 371 (c)(1),
(2) Date: Dec. 2, 2021

(87) PCT Pub. No.: WO2021/095500
PCT Pub. Date: May 20, 2021

(65) Prior Publication Data
US 2022/0327707 A1 Oct. 13, 2022

(30) Foreign Application Priority Data
Nov. 12, 2019 (JP) .................................. 2019-204969

(51) Int. Cl.
G06T 7/00 (2017.01)
A61B 1/00 (2006.01)
(Continued)

(52) U.S. Cl.
CPC ...... *G06T 7/0016* (2013.01); *A61B 1/000096* (2022.02); *G16H 30/40* (2018.01);
(Continued)

(58) Field of Classification Search
CPC ......... G06T 7/0016; G06T 2207/10068; G06T 2207/20081; G06T 2207/20084;
(Continued)

(56) References Cited

U.S. PATENT DOCUMENTS 9,646,265 B2 * 5/2017 Ando ..................... G06Q 10/04
11,107,215 B2 * 8/2021 Ahn ..................... G06F 18/285
(Continued)

FOREIGN PATENT DOCUMENTS

JP 2007-000428 1/2007
JP 2019-159876 9/2019
(Continued)

OTHER PUBLICATIONS

Sep. 6, 2022 Japanese Office Action issued in corresponding Japanese Patent Application No. 2019-204969.
(Continued)

*Primary Examiner* — Dhaval V Patel
(74) *Attorney, Agent, or Firm* — GREENBLUM & BERNSTEIN, P.L.C.

(57) ABSTRACT

A program causes a computer to execute processing including: acquiring an endoscope image captured by an endoscope; inputting the acquired endoscope image into a plurality of learning models learned so as to output diagnosis support information regarding a lesion included in the endoscope image; acquiring a plurality of pieces of diagnosis support information output from each of the learning models; and outputting a plurality of pieces of the acquired diagnosis support information and information regarding each of the learning models in association with each other. Alternatively, the program causes the computer to execute the processing of inputting the acquired endoscope image into one learning model, executing a plurality of determination logics to acquire a plurality of pieces of output diagnosis support information, and outputting a plurality of pieces of the acquired diagnosis support information and information regarding each of the learning models in association with each other is executed.

8 Claims, 15 Drawing Sheets

(51) Int. Cl.
  *G16H 30/40* (2018.01)
  *G16H 50/20* (2018.01)

(52) U.S. Cl.
  CPC ... *G16H 50/20* (2018.01); *G06T 2207/10068* (2013.01); *G06T 2207/20081* (2013.01); *G06T 2207/20084* (2013.01); *G06T 2207/30096* (2013.01)

(58) Field of Classification Search
  CPC ......... G06T 2207/30096; G06T 7/0012; A61B 1/000096; A61B 1/000094; A61B 1/0005; G16H 30/40; G16H 50/20; G16H 50/70
  See application file for complete search history.

(56) References Cited

U.S. PATENT DOCUMENTS

| | | | | |
|---|---|---|---|---|
| 11,430,140 B2 * | 8/2022 | Cho | ........................ | G06N 3/045 |
| 11,741,361 B2 * | 8/2023 | Zheng | ................... | H04L 41/145 |
| | | | | 706/26 |
| 11,748,612 B2 * | 9/2023 | Lee | .......................... | G06N 5/04 |
| | | | | 706/25 |
| 2014/0101080 A1 | 4/2014 | Lee et al. | | |
| 2016/0073958 A1 | 3/2016 | Kang et al. | | |
| 2019/0034800 A1 | 1/2019 | Shiratani | | |
| 2020/0279652 A1 | 9/2020 | Nenoki et al. | | |
| 2021/0327583 A1 * | 10/2021 | Harte | ..................... | G16H 30/40 |

FOREIGN PATENT DOCUMENTS

| | | |
|---|---|---|
| WO | 2017/175282 | 10/2017 |
| WO | 2019/102950 | 5/2019 |

OTHER PUBLICATIONS

International Search Report issued in International Bureau of WIPO Patent Application No. PCT/JP2020/040092, dated Jan. 26, 2021, along with an English translation thereof.

* cited by examiner

FIG. 6

| LEARNING MODEL NAME | VERSION NUMBER | APPLICATION DATE | CHANGE | CUMULATIVE NUMBER OF USES |
|---|---|---|---|---|
| NN-1 | 1.0 | MAY 1, 2019 | null | 50 |
| NN-2 | 1.1 | JUNE 1, 2019 | ADDED TRAINING DATA AND RELEARNED | 120 |
| NN-3 | 1.2 | JULY 1, 2019 | ADDED TRAINING DATA REGARDING LESION OF CANCER AND RELEARNED | 150 |
| NN-4 | 2.0 | AUGUST 1, 2019 | INCREASED NUMBER OF INTERMEDIATE LAYERS | 30 |
| NN-5 | 2.1 | AUGUST 8, 2019 | ADDED TRAINING DATA AND RELEARNED | 80 |

FIG. 8

= DISPLAY SCREEN OF DIAGNOSIS SUPPORT INFORMATION =

| LEARNING MODEL NAME | NN-1 | NN-2 | NN-3 | NN-4 | NN-5 |
|---|---|---|---|---|---|
| VERSION | 1.0 | 1.1 | 1.2 | 2.0 | 2.1 |
| APPLICATION DATE | MAY 1, 2019 | JUNE 1, 2019 | JULY 1, 2019 | AUGUST 1, 2019 | AUGUST 8, 2019 |
| CHANGE | null | ADDED TRAINING DATA AND RELEARNED | ADDED TRAINING DATA REGARDING LESION OF CANCER AND RELEARNED | INCREASED NUMBER OF INTERMEDIATE LAYERS | ADDED TRAINING DATA AND RELEARNED |
| | LESION: ABSENT | LESION: ABSENT | LESION: PRESENT SYMPTOM: CANCER STAGE: 5 | LESION: PRESENT SYMPTOM: CANCER STAGE: 3 | LESION: ABSENT |

FIG. 11

= DISPLAY SCREEN OF DIAGNOSIS SUPPORT INFORMATION =

| VERSION | 1.0 | 1.1 | 1.2 | 2.0 | 2.0 |
|---|---|---|---|---|---|
| APPLICATION DATE | MAY 1, 2019 | JUNE 1, 2019 | JULY 1, 2019 | AUGUST 1, 2019 | AUGUST 8, 2019 |
| CHANGE | null | ADDED TRAINING DATA AND RELEARNED | ADDED TRAINING DATA REGARDING LESION OF CANCER AND RELEARNED | INCREASED NUMBER OF INTERMEDIATE LAYERS | ADDED TRAINING DATA AND RELEARNED |
| IMAGE CAPTURING DATE AUGUST 1, 2019  | LESION: ABSENT | LESION: ABSENT | LESION: PRESENT SYMPTOM: CANCER STAGE: 5 | LESION: PRESENT SYMPTOM: CANCER STAGE: 3 | LESION: ABSENT |
| IMAGE CAPTURING DATE JULY 25, 2019  | LESION: ABSENT | LESION: ABSENT | LESION: PRESENT SYMPTOM: CANCER STAGE: 2 | LESION: PRESENT SYMPTOM: CANCER STAGE: 1 | LESION: ABSENT |
| IMAGE CAPTURING DATE JUNE 1, 2019  | LESION: ABSENT | LESION: ABSENT | LESION: PRESENT SYMPTOM: CANCER STAGE: 1 | LESION: ABSENT | LESION: ABSENT |

FIG. 14

= SCREEN FOR SELECTING LEARNING MODEL TO BE USED =

| LEARNING MODEL NAME | VERSION NUMBER | APPLICATION DATE | CHANGE | CUMULATIVE NUMBER OF USES | USE |
|---|---|---|---|---|---|
| NN-1 | 1.0 | MAY 1, 2019 | null | 50 | ☐ |
| NN-2 | 1.1 | JUNE 1, 2019 | ADDED TRAINING DATA AND RELEARNED | 120 | ☑ |
| NN-3 | 1.2 | JULY 1, 2019 | ADDED TRAINING DATA REGARDING LESION OF CANCER AND RELEARNED | 150 | ☑ |
| NN-4 | 2.0 | AUGUST 1, 2019 | INCREASED NUMBER OF INTERMEDIATE LAYERS | 30 | ☐ |
| NN-5 | 2.1 | AUGUST 8, 2019 | ADDED TRAINING DATA AND RELEARNED | 80 | ☑ |

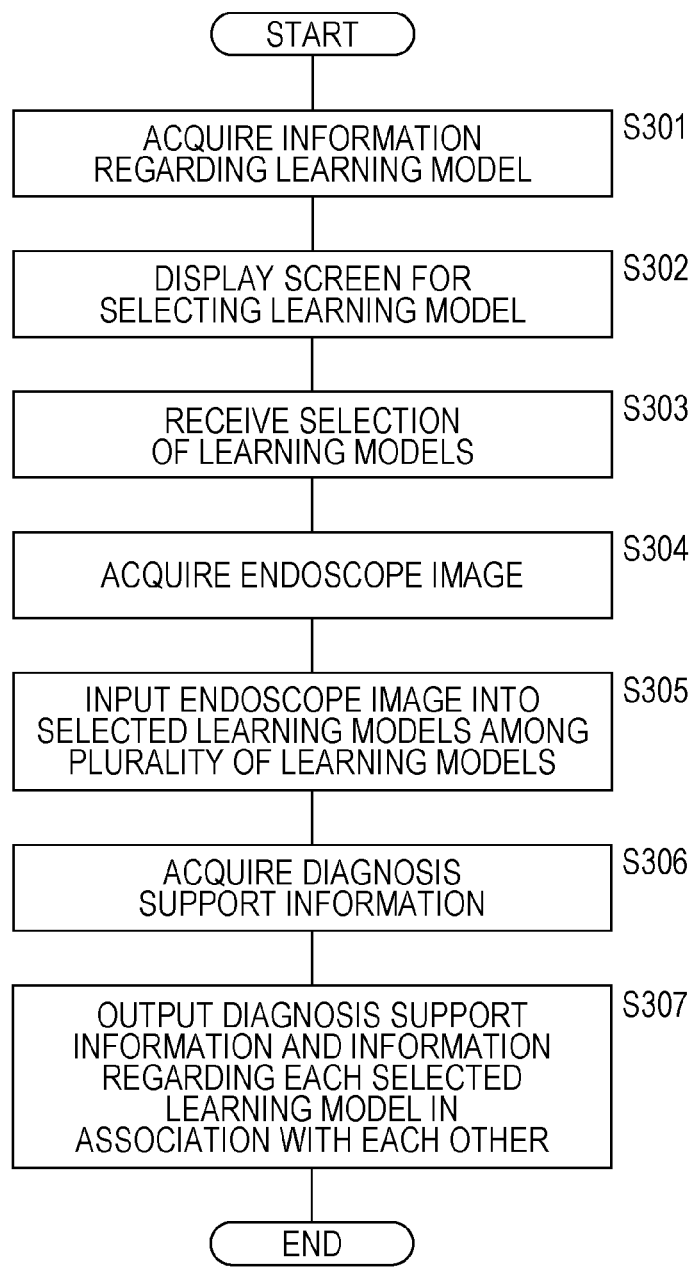

PROGRAM, INFORMATION PROCESSING METHOD, AND INFORMATION PROCESSING DEVICE

TECHNICAL FIELD

The present technology relates to a program, an information processing method, and an information processing apparatus.

The present application claims priority based on Japanese Patent Application No. 2019-204969 filed on Nov. 12, 2019, the entire contents of which are incorporated herein by reference.

BACKGROUND ART

There has been developed computer-aided diagnostic technology that uses a learning model to automatically detect lesion sites from medical images such as endoscope images. There is known a method of generating a learning model by machine learning using training data in which a correct answer label is assigned to an endoscope image including a lesion site (for example, Patent Literature 1).

CITATION LIST

Patent Literature

Patent Literature 1: WO 2017/175282 A

SUMMARY OF INVENTION

Technical Problem

The generated learning model may be relearned thereafter. The relearned learning model is a learning model changed from the original learning model and is assumed to output a result different from that of the original learning model. However, the learning model described in Patent Literature 1 does not consider a difference between results output from the learning models before and after the relearning.

In one aspect, an object of the present invention is to provide a program and the like capable of grasping an influence caused by a change of a learning model that outputs information regarding diagnosis support even in a case where the learning model is changed.

Solution to Problem

A program according to an aspect of the present disclosure causes a computer to execute processing including: acquiring an endoscope image captured by an endoscope; inputting the acquired endoscope image into a plurality of learning models learned so as to output diagnosis support information regarding a lesion included in the endoscope image; acquiring a plurality of pieces of diagnosis support information output from each of the plurality of learning models; and outputting a plurality of pieces of the acquired diagnosis support information and information regarding each of the plurality of learning models in association with each other.

A program according to an aspect of the present disclosure causes a computer to execute processing including: acquiring an endoscope image captured by an endoscope; inputting the acquired endoscope image into a learning model learned so as to output diagnosis support information regarding a lesion included in the endoscope image; executing a plurality of diagnostic logics on the learning model to acquire a plurality of pieces of output diagnosis support information; and outputting a plurality of pieces of the acquired diagnosis support information and information regarding each of the plurality of diagnostic logics executed on the learning model that is information regarding each of the plurality of learning models in association with each other.

An information processing method according to an aspect of the present disclosure causes a computer to execute processing including: acquiring an endoscope image captured by an endoscope; inputting the acquired endoscope image into a plurality of learning models learned so as to output diagnosis support information regarding a lesion included in the endoscope image; acquiring a plurality of pieces of diagnosis support information output from each of the plurality of learning models; and outputting a plurality of pieces of the acquired diagnosis support information and information regarding each of the plurality of learning models in association with each other.

An information processing apparatus according to an aspect of the present disclosure includes: an acquisition unit that acquires an endoscope image captured by an endoscope; an input unit that inputs the acquired endoscope image into a plurality of learning models learned so as to output diagnosis support information regarding a lesion included in the endoscope image; and an output unit that acquires a plurality of pieces of diagnosis support information output from each of the plurality of learning models and outputs a plurality of pieces of the acquired diagnosis support information and information regarding each of the plurality of learning models in association with each other. Alternatively, diagnosis support information of a plurality of diagnostic logics is output by one learning model and there is a provided an output unit that outputs in association with a plurality of the acquired diagnosis support information.

Advantageous Effects of Invention

According to the present disclosure, it is possible to provide a program and the like capable of grasping an influence caused by a change of a learning model that outputs information regarding diagnosis support even in a case where the learning model is changed.

BRIEF DESCRIPTION OF DRAWINGS

FIG. 6 is an explanatory diagram exemplifying a data layout of a learning model management DB.

FIG. 7 is a functional block diagram exemplifying functional parts included in a control unit of the information processing apparatus or the like.

FIG. 8 is an explanatory diagram illustrating an example of a screen (display screen of diagnosis support information) output to a display unit.

FIG. 11 is an explanatory diagram illustrating an example of a screen (result display screen) output to a display unit.

FIG. 14 is an explanatory diagram illustrating an example of a screen (screen for selecting a learning model) output to a display unit.

FIG. 15 is a flowchart illustrating an example of a processing procedure performed by the control unit of the information processing apparatus.

DESCRIPTION OF EMBODIMENTS

First Embodiment

Figure 1:
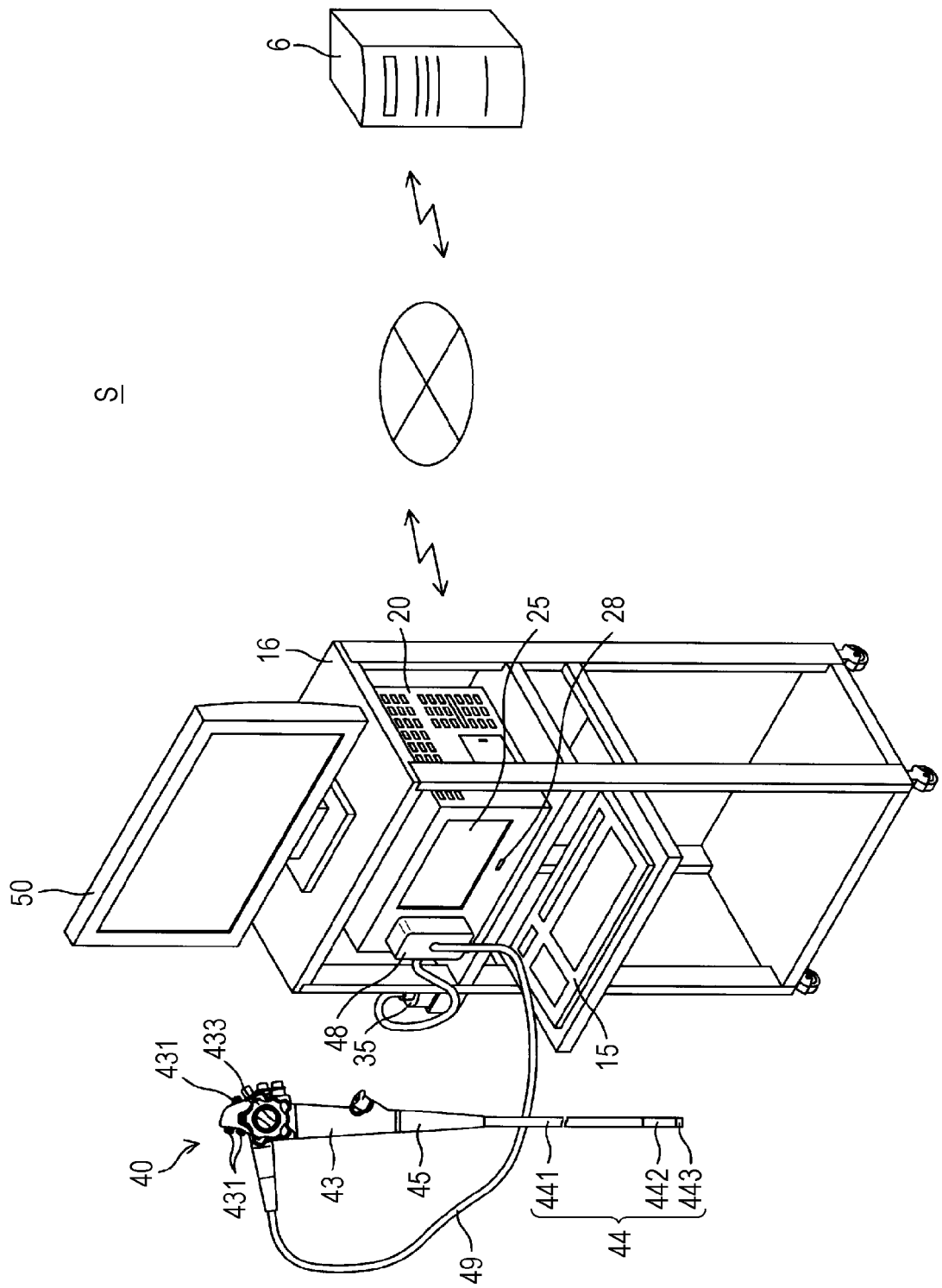
FIG. 1 is a schematic diagram illustrating an outline of a diagnosis support system according to a first embodiment.

Hereinafter, the present invention will be specifically described with reference to the drawings illustrating embodiments of the present invention. FIG. 1 is a schematic diagram illustrating an outline of a diagnosis support system S according to a first embodiment. The diagnosis support system S includes an endoscope device 10 and an information processing apparatus 6 communicably connected to the endoscope device 10.

The endoscope device 10 transmits an image (captured image) captured by an image sensor of an endoscope 40 to a processor for an endoscope 20, and the processor for an endoscope 20 performs various types of image processing such as gamma correction, white balance correction, and shading correction, thereby generating an endoscope image easily visible by an operator. The endoscope device 10 outputs (transmits) the generated endoscope image to the information processing apparatus 6. The information processing apparatus 6 that has acquired the endoscope image transmitted from the endoscope device 10 performs various types of information processing on the basis of these endoscope images and outputs information regarding diagnosis support.

The endoscope device 10 includes the processor for an endoscope 20, an endoscope 40, and a display device 50. The display device 50 is, for example, a liquid crystal display device or an organic electro luminescence (EL) display device.

The display device 50 is installed on the upper stage of a storage shelf 16 with casters. The processor for an endoscope 20 is housed in the middle stage of the storage shelf 16. The storage shelf 16 is disposed in the vicinity of a bed for an endoscopic examination (not illustrated). The storage shelf 16 includes a pull-out shelf on which a keyboard 15 connected to the processor for an endoscope 20 is mounted.

The processor for an endoscope 20 has a substantially rectangular parallelepiped shape and includes a touch panel 25 provided on one surface thereof. A reading unit 28 is disposed at the bottom of the touch panel 25. The reading unit 28 is a connection interface for performing reading and writing on a portable recording medium such as a universal serial bus (USB) connector, a secure digital (SD) card slot, a compact disc read only memory (CD-ROM) drive, or the like.

The endoscope 40 includes an insertion portion 44, an operation unit 43, a universal cord 49, and a scope connector 48. The operation unit 43 is provided with a control button 431. The insertion portion 44 is long and has one end connected to the operation unit 43 via a bend preventing portion 45. The insertion portion 44 includes a soft portion 441, a bending section 442, and a distal tip 443 in order from a side of the operation unit 43. The bending section 442 is bent according to the operation of a bending knob 433. Physical detection devices such as a three-axis acceleration sensor, a gyro sensor and a geomagnetic sensor or a magnetic coil sensor may be mounted on the insertion portion 44, and when the endoscope 40 is inserted into the body of a subject, detection results from these physical detection devices may be acquired.

The universal cord 49 is long and has a first end connected to the operation unit 43 and a second end connected to the scope connector 48. The universal cord 49 is soft. The scope connector 48 has a substantially rectangular parallelepiped shape. The scope connector 48 is provided with an air supply/water supply metal port 36 (see FIG. 2) for connecting an air supply/water supply tube.

Figure 2:
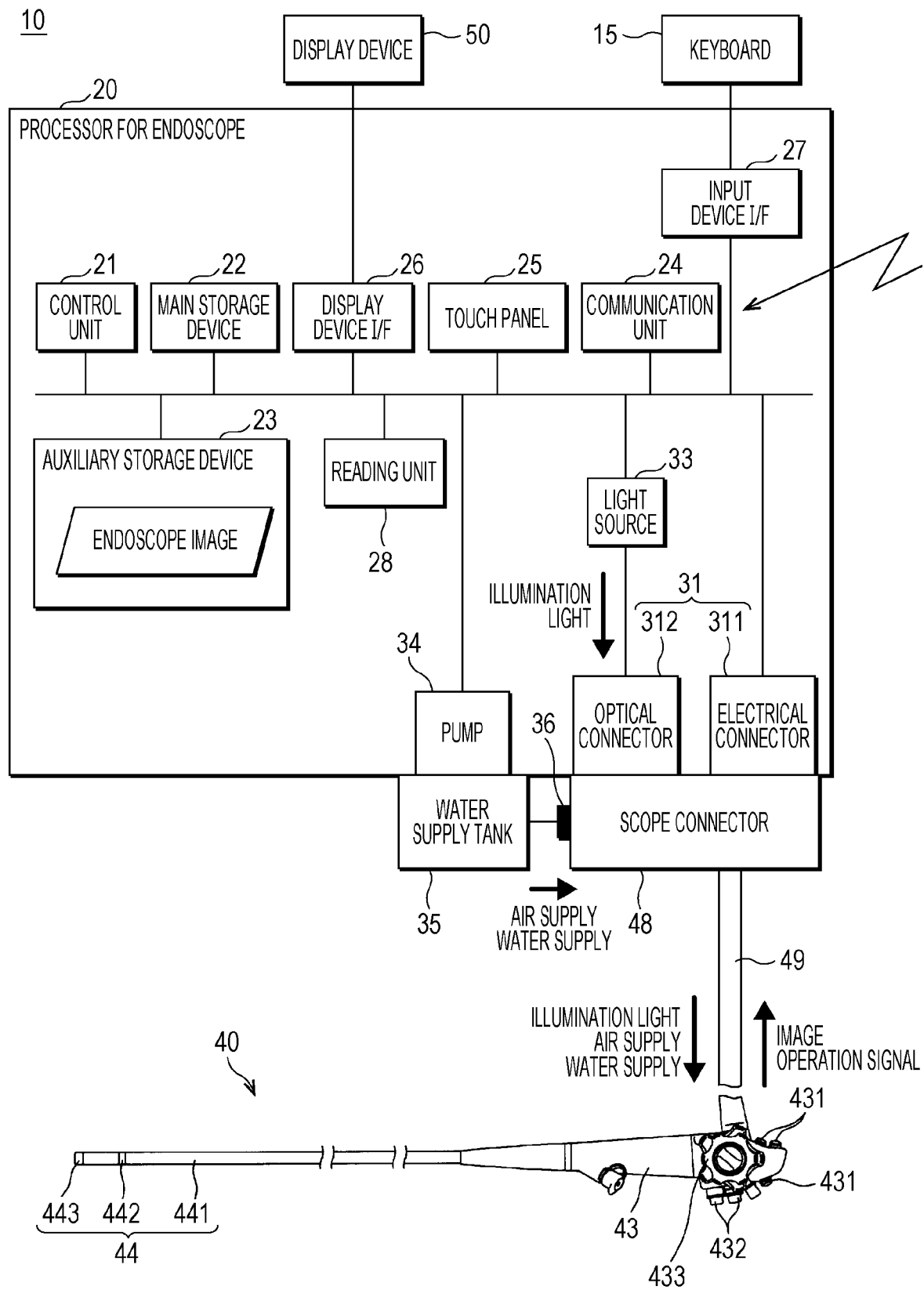
FIG. 2 is a block diagram illustrating a configuration example of an endoscope device included in the diagnosis support system.

FIG. 2 is a block diagram illustrating a configuration example of the endoscope device 10 included in the diagnosis support system S. The control unit 21 is an arithmetic control device that executes a program of the present embodiment. One or a plurality of central processing units (CPUs), graphics processing units (GPUs), multi-core CPUs or the like is used for the control unit 21. The control unit 21 is connected to each hardware unit constituting the processor for an endoscope 20 via a bus.

The main storage device 22 is, for example, a storage device such as a static random access memory (SRAM), a dynamic random access memory (DRAM), or a flash memory. The main storage device 22 temporarily stores information necessary in the middle of processing performed by the control unit 21 and a program being executed by the control unit 21. An auxiliary storage device 23 is, for example, a storage device such as an SRAM, a flash memory, or a hard disk and is a storage device having a capacity larger than that of the main storage device 22. In the auxiliary storage device 23, for example, the acquired captured image and the generated endoscope image may be stored as intermediate data.

A communication unit 24 is a communication module or a communication interface for performing communication with the information processing apparatus 6 via a network in a wired or wireless manner and is, for example, a narrow-area wireless communication module such as Wi-Fi (registered trademark) or Bluetooth (registered trademark) or a wide-area wireless communication module such as 4G or Long Term Evolution (LTE). The touch panel 25 includes a display unit 7 such as a liquid crystal display panel and an input unit 8 layered on the display unit 7.

A display device I/F 26 is an interface for connecting the processor for an endoscope 20 and the display device 50. An input device I/F 27 is an interface for connecting the processor for an endoscope 20 and an input device such as the keyboard 15.

A light source 33 is a high-luminance white light source such as a while light emitting diode (LED) or a xenon lamp.

The light source 33 is connected to the bus via a driver (not illustrated). The turning on and off of the light source 33 and the change of luminance are controlled by the control unit 21. Illumination light emitted from the light source 33 is incident on an optical connector 312. The optical connector 312 engages with the scope connector 48 to supply the illumination light to the endoscope 40.

A pump 34 generates pressure for the air supply and water supply function of the endoscope 40. The pump 34 is connected to the bus via a driver (not illustrated). The turning on and off of the pump 34 and the change of pressure are controlled by the control unit 21. The pump 34 is connected to the air supply/water supply metal port 36 provided in the scope connector 48 via a water supply tank 35.

The function of the endoscope 40 connected to the processor for an endoscope 20 will be outlined. A fiber bundle, a cable bundle, an air supply tube, a water supply tube, and the like are inserted inside the scope connector 48, the universal cord 49, the operation unit 43, and the insertion portion 44. The illumination light emitted from the light source 33 is emitted from an illumination window provided at the distal tip 443 via the optical connector 312 and the fiber bundle. A range illuminated by the illumination light is captured as an image by an image sensor provided at the distal tip 443. The captured image is transmitted from the image sensor to the processor for an endoscope 20 via the cable bundle and an electrical connector 311.

The control unit 21 of the processor for an endoscope 20 executes a program stored in the main storage device 22, thereby functioning as an image processing unit 211. The image processing unit 211 performs various types of image processing such as gamma correction, white balance correction, and shading correction on an image (captured image) output from the endoscope 40 and outputs the image as the endoscope image.

Figure 3:
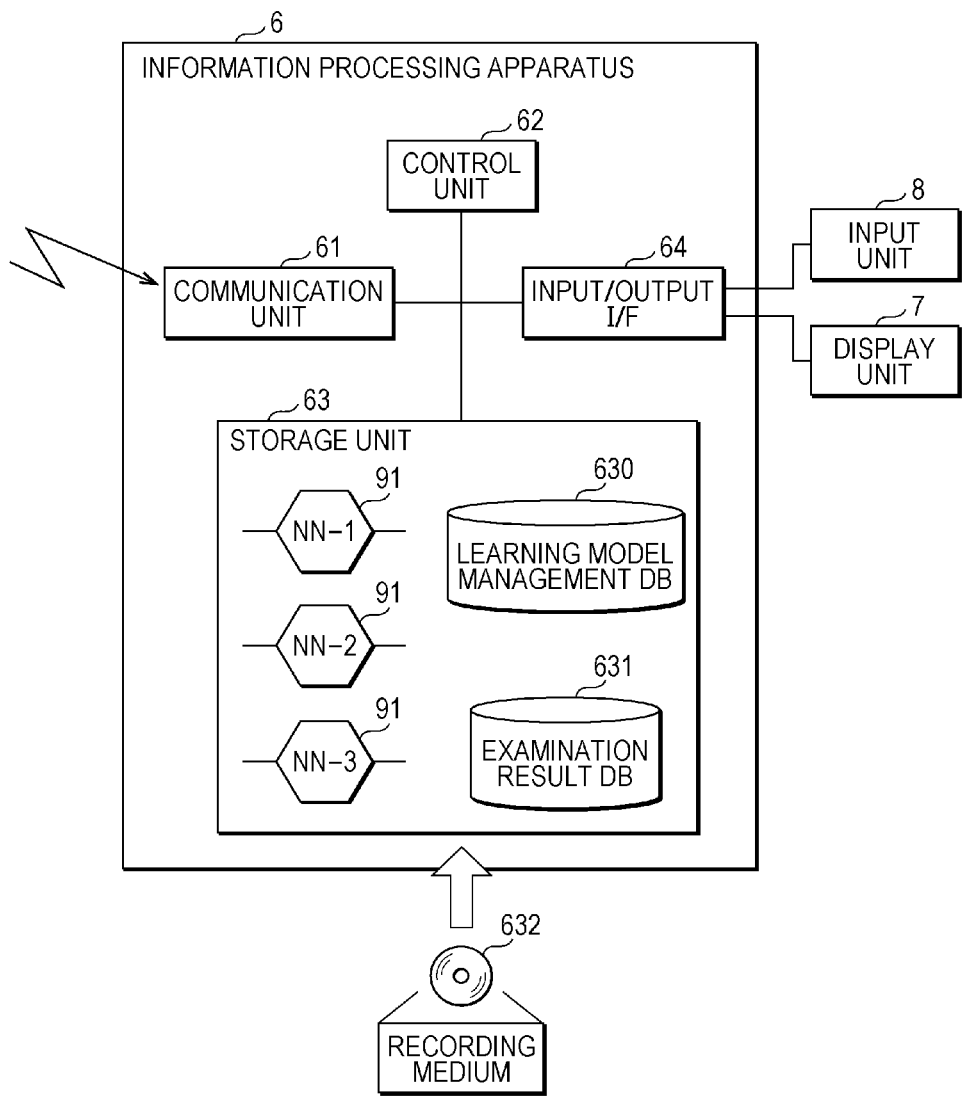
FIG. 3 is a block diagram illustrating a configuration example of an information processing apparatus included in the diagnosis support system.

FIG. 3 is a block diagram illustrating a configuration example of the information processing apparatus 6 included in the diagnosis support system S. The information processing apparatus 6 includes a control unit 62, a communication unit 61, a storage unit 63, and an input/output I/F 64. The information processing apparatus 6 is, for example, a server device, a personal computer, or the like. The server device includes not only a single server device but also a cloud server device or a virtual server device including a plurality of computers. The information processing apparatus 6 may be provided as a cloud server located on an external network accessible from the processor for an endoscope 20.

The control unit 62 includes one or a plurality of arithmetic processing devices having a time counting function, such as central processing units (CPUs), micro-processing units (MPUs), and graphics processing units (GPUs) and reads and executes a program P stored in the storage unit 63, thereby performing various types of information processing, control processing, and the like related to the information processing apparatus 6. Alternatively, the control unit 62 may include a quantum computer chip, and the information processing apparatus 6 may be a quantum computer.

The storage unit 63 includes a volatile storage area such as a static random access memory (SRAM), a dynamic random access memory (DRAM), or a flash memory and a nonvolatile storage area such as an electrically erasable and programmable read only memory (EEPROM) or a hard disk. The storage unit 63 stores in advance the program P and data to be referred to at the time of processing. The program P stored in the storage unit 63 may be a program that stores a program P read from a recording medium 632 readable by the information processing apparatus 6. In addition, the program P may be a program downloaded from an external computer (not illustrated) connected to a communication network (not illustrated) and be stored in the storage unit 63. The storage unit 63 stores an entity file (instance file of a neural network (NN)) constituting each of a plurality of learning models 91 to be described later. These entity files may be configured as a part of the program P. The storage unit 63 may store an examination result database (DB) 631 and a learning model management DB 630 to be described later.

The communication unit 61 is a communication module or a communication interface for performing communication with the endoscope device 10 in a wired or wireless manner and is, for example, a narrow-area wireless communication module such as Wi-Fi (registered trademark) or Bluetooth (registered trademark) or a wide-area wireless communication module such as 4G or LTE.

The input/output I/F 64 is compliant, for example, with a communication standard such as USB or D-subminiature (DSUB) and is a communication interface for performing serial communication with an external device connected to the input/output I/F 64. For example, a display unit 7 such as a display and an input unit 8 such as the keyboard 15 are connected to the input/output I/F 64, and the control unit 62 outputs, to the display unit 7, a result of information processing performed on the basis of an execution command or an event input from the input unit 8.

Figure 4:
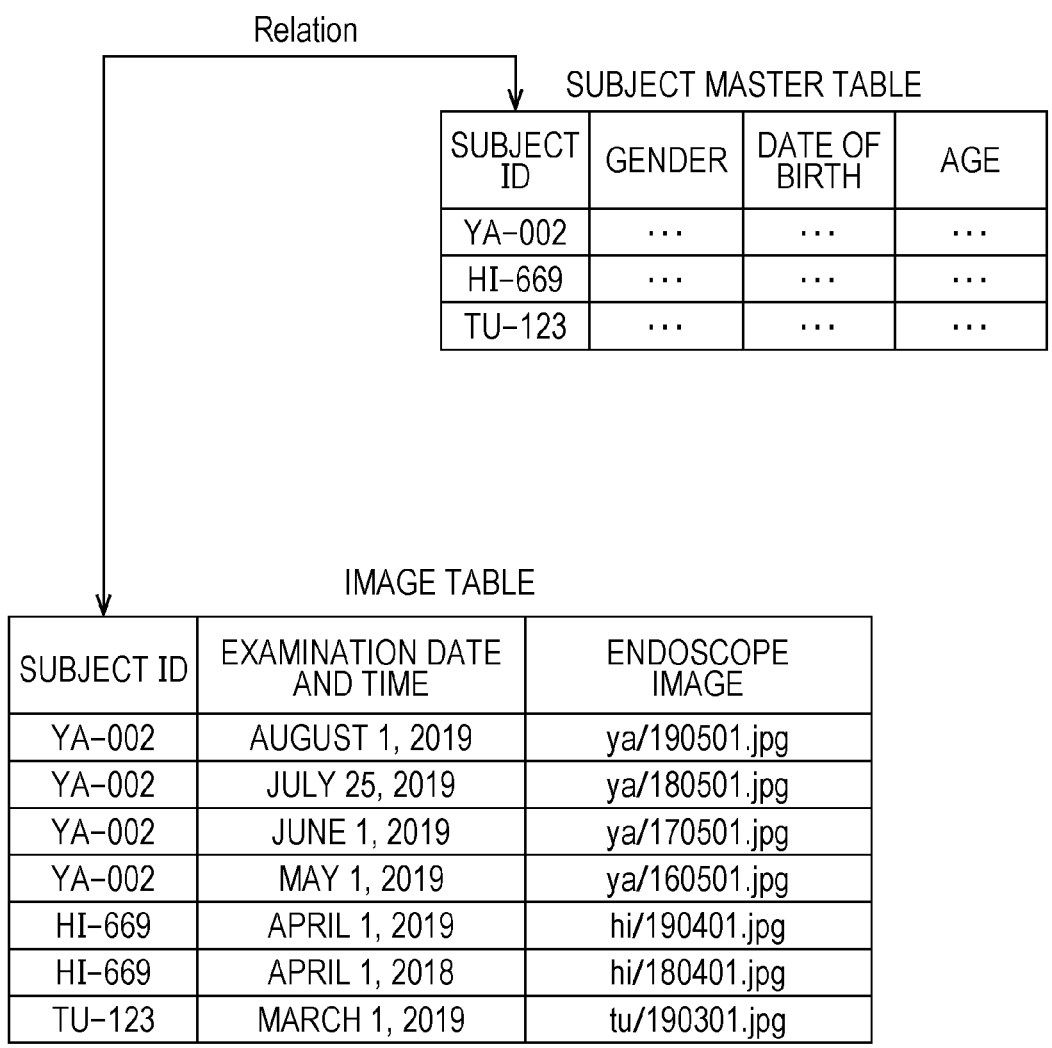
FIG. 4 is an explanatory diagram exemplifying a data layout of an examination result DB.

FIG. 4 is an explanatory diagram exemplifying a data layout of the examination result DB 631. The examination result DB 631 is stored in the storage unit 63 of the information processing apparatus 6 and includes database management software such as a relational database management system (RDBMS) implemented in the information processing apparatus 6. The information processing apparatus 6 may acquire the endoscope image, an examination date and time, and the attribute information of the subject output by the processor for an endoscope 20 and register the acquired endoscope image, the examination date and time, and the attribute information of the subject in the examination result DB 631.

The examination result DB 631 includes, for example, a subject master table and an image table, and the subject master table and the image table are set to be associated with each other by a subject ID that is an item (metadata) included in both the tables.

The subject master table includes, for example, the subject ID, a gender, a date of birth, and an age as management items (metadata). In the item (field) of the subject ID, ID information is stored in order to uniquely specify the subject who has undergone an endoscopic examination. In the items (fields) of the gender and the date of birth, and the age, biological attributes that are a gender and a date of birth corresponding to the subject ID are stored, and in the item (field) of the age, the age at a current time point calculated on the basis of the date of birth is stored. The gender and the age are managed as biological information of the subject by the subject master table.

Figure 5:
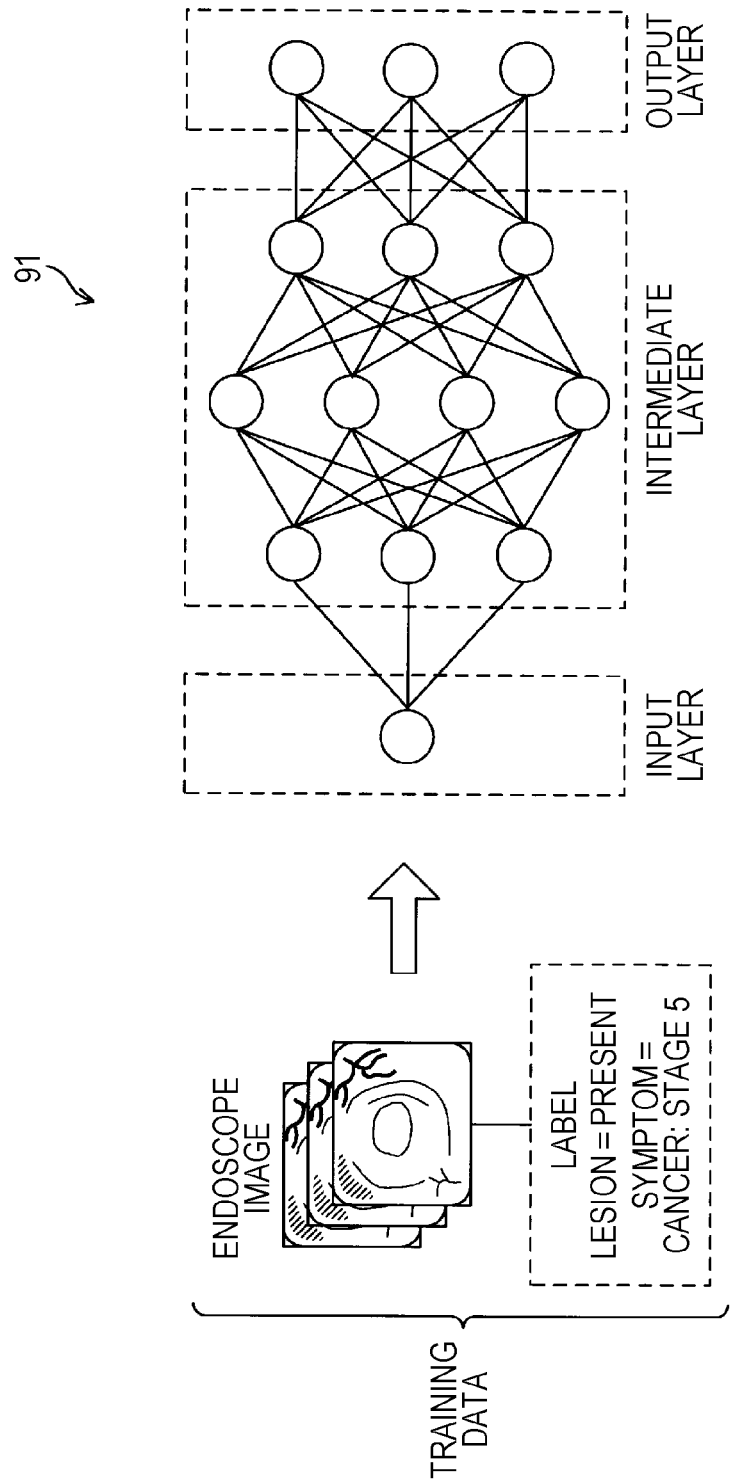
FIG. 5 is an explanatory diagram regarding generation processing of a learning model.

FIG. 5 is an explanatory diagram regarding generation processing of the learning model 91. The information processing apparatus 6 constructs (generates) a neural network that learns on the bases of training data in which an endoscope image is used as problem data and diagnosis support information including at least one of the presence or absence of a lesion, the type of symptom of the lesion, a stage of symptom of the lesion, a location of the lesion, and the like is used as answer data, thereby inputting the endoscope image and outputting the diagnosis support information including the presence or absence of a lesion and the like. The endoscope image includes, for example, an intracorporeal site suspected of being a lesion. The presence or absence of a lesion, the type of a symptom, a stage of the symptom, and a location of the lesion are information regarding the presence or absence of a lesion, the type of symptom, a stage of symptom, and a location of the lesion regarding the intracorporeal site included in the endoscope image.

The neural network (learning model 91) learned using the training data is assumed to be used as a program module that is a part of artificial intelligence software. The learning model 91 is used in the information processing apparatus 6 including the control unit 62 (CPU or the like) and the storage unit 63 as described above and is executed by the information processing apparatus 6 having arithmetic processing capability in this way, whereby a neural network system is configured. That is, the control unit 62 of the information processing apparatus 6 operates to perform an arithmetic operation of extracting a feature amount of the endoscope image input into an input layer according to a command from the learning model 91 stored in the storage unit 63 and output the diagnosis support information including the presence or absence of a lesion and the like from an output layer.

The input layer has a plurality of neurons that receives the input of a pixel value of the endoscope image, and the input layer transmits the input pixel value and distance information to the intermediate layer. The intermediate layer has a plurality of neurons that extracts an image feature amount of the endoscope image, and the intermediate layer transfers the extracted image feature amount to the output layer. The output layer has one or a plurality of neurons that outputs information regarding the presence or absence of a lesion and the stage of a symptom, and the output layer outputs information regarding the presence or absence of a lesion and the stage of a symptom on the basis of the image feature amount output from the intermediate layer. For example, in a case where the learning model 91 is a convolutional neural network (CNN), the intermediate layer has a configuration in which a convolution layer that convolves the pixel value of each pixel input from the input layer and a pooling layer that maps (compresses) the pixel value convolved by the convolution layer are alternately connected, and the intermediate layer finally extracts the feature amount of the endoscope image while compressing pixel information of the endoscope image. The output layer has one or a plurality of neurons that outputs information regarding the presence or absence of a lesion and the like in the intracorporeal site included in the endoscope image, and the output layer outputs information regarding the presence or absence of a lesion on the basis of the image feature amount and the like output from the intermediate layer. The output information regarding the presence or absence of a lesion and the like is information used as diagnosis support information by a doctor or the like who operates the endoscope 40.

In the present embodiment, data input into the learning model 91 is described as the endoscope image, but the present invention is not limited thereto. The data input into the learning model 91 may be a captured image (raw image) captured by the image sensor of the endoscope 40. That is, the learning model 91 may output information regarding the presence or absence of a lesion and the like when the captured image is input.

In the present embodiment, the learning model 91 is described as a neural network (NN) such as a CNN, but the learning model 91 is not limited to the NN and may be a learning model 91 including another learning algorithm such as a support vector machine (SVM), a Bayesian network, or a regression tree. Alternatively, instead of the CNN, any object detection algorithm such as Regions with Convolutional Neural Network (RCNN), Fast RCNN, Faster RCNN, Single Shot Multibook Detector (SSD), or You Only Look Once (YOLO) may be used.

The information processing apparatus 6 compares a value output from the output layer with information (the presence or absence of a lesion, the type of a symptom, the stage of the symptom) labeled for the problem data (endoscope image), that is, a correct answer value (answer data) and optimizes parameters used for arithmetic processing in the intermediate layer so that the output value from the output layer approaches the correct answer value. The parameters are, for example, a weight (coupling coefficient) between neurons, a coefficient of an activation function used in each neuron, and the like. A parameter optimization method is not particularly limited, but for example, the information processing apparatus 6 optimizes various parameters using a back propagation method. The information processing apparatus 6 performs the above processing on the endoscope image included in the training data, generates the learning model 91, and stores the generated learning model 91 in the storage unit 63.

The endoscope image (problem data) used as the training data and the information (answer data) regarding the presence or absence of a lesion and the like correlated with these pieces of information are stored in a large amount as result data of an endoscopic examination performed in each medical institution, and these pieces of result data can be used to generate a large amount of training data for learning the learning model 91.

The learning model 91 that outputs the presence or absence of a lesion and the like by inputting an endoscope image is caused to learn, for example, using different training data, whereby a plurality of learning models 91 is generated. As described above, the endoscope image (problem data) constituting the training data and a data set based on the information (answer data) regarding the presence or absence of a lesion and the like are accumulated every day in each medical institution. The latest training data includes the accumulated data sets, and in some cases, the existing (generated) learning model 91 is relearned using the latest training data. For example, even in the case of a neural network using the same layer configuration and activation function, training data is different. Therefore, a plurality of learning models 91 having slightly different output results is generated by such relearning. That is, in a case where the training data is updated in a cycle of, for example, about one month, a plurality of pieces of training data corresponding to the update time point is configured as a version difference. In this way, learning is performed using each piece of training data configured as a version difference, whereby a plurality of learning models 91 corresponding to the version can be generated.

To generate the plurality of learning models 91, learning is performed using different training data for the neural network using the same layer configuration and activation function, but the present invention is not limited thereto. A plurality of learning models 91 may be generated by causing a neural network having a different layer configuration or a different configuration form of an activation function or the like to learn using the same training data. Alternatively, a plurality of learning models 91 may be generated by causing a neural network having a different layer configuration or a different configuration form of an activation function or the like to learn using different training data.

FIG. 6 is an explanatory diagram exemplifying a data layout of the learning model management DB 630. The learning model management DB 630 includes, for example, a learning model name, a version number, an application date, a change, and the cumulative number of uses as management items (metadata).

In the item (field) of the learning model name, for example, a model name for identifying each of the plurality of learning models 91 is stored. In the item (field) of the version number, for example, a version number of the training data used to generate the learning model 91 is stored. Alternatively, a version number of the learning model 91 itself may be stored.

In the item (field) of the application date, for example, a date on which the generated learning model 91 was applied (incorporated) to the diagnosis support system S and the learning model 91 became available in the diagnosis support system S is stored. An operator of the endoscope 40 such as a doctor can grasp an application period of the learning model 91 up until the present by referring to the application date of each learning model 91.

In the item (field) of the change, for example, a matter regarding a change compared with a learning model 91 of the previous version is stored. The operator of the endoscope 40 such as a doctor can grasp matters regarding the history of the plurality of learning models 91 by referring to the change.

In the item (field) of the cumulative number of uses, for example, the cumulative number of uses for each learning model 91 up to the current time point is stored. The operator of the endoscope 40 such as a doctor can grasp the use records or popularity of each of the plurality of learning models 91 by referring to the cumulative number of uses.

Figure 7:
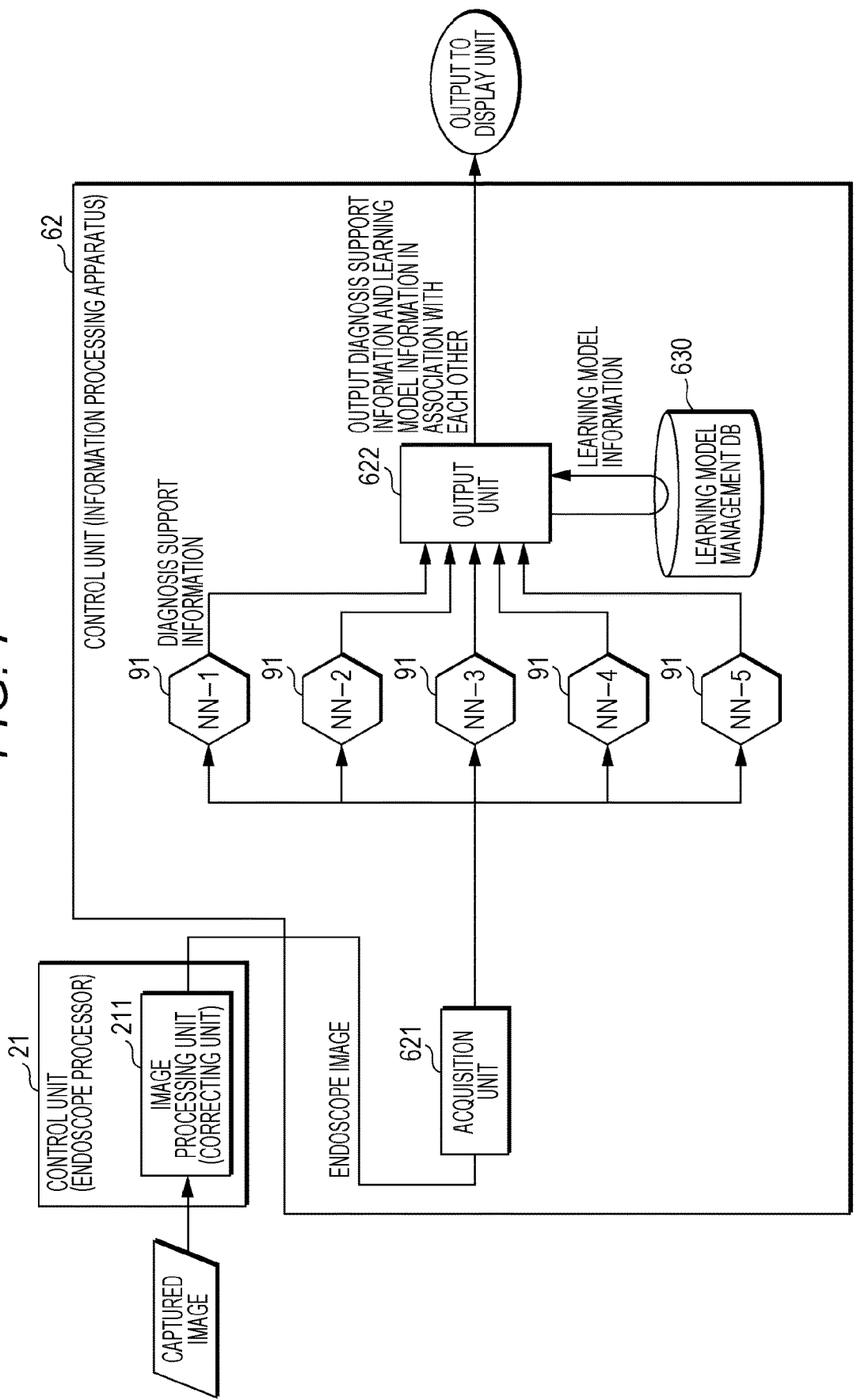

FIG. 7 is a functional block diagram exemplifying functional parts included in the control unit 62 of the information processing apparatus 6 or the like. The control unit 21 of the processor for an endoscope 20 (endoscope device 10) executes the program stored in the main storage device 22, thereby functioning as the image processing unit 211. The control unit 62 of the information processing apparatus 6 executes the program P stored in the storage unit 63, thereby functioning as an acquisition unit 621 and an output unit 622. In addition, the control unit 62 executes the program P stored in the storage unit 63 or reads each entity file constituting each of the plurality of learning models 91 (NN-1 and NN-2 to NN-5), thereby functioning as the plurality of learning models 91.

The image processing unit 211 performs various types of image processing such as gamma correction, white balance correction, and shading correction on the image (captured image) output from the endoscope 40, and outputs the image as the endoscope image. The image processing unit 211 outputs (transmits) the generated endoscope image to the information processing apparatus 6. The image processing unit 211 may further output the subject ID input from the keyboard 15 to the information processing apparatus 6.

The acquisition unit 621 acquires the endoscope image output by the processor for an endoscope 20 and outputs the acquired endoscope image to each of the plurality of learning models 91. In a case where the acquisition unit 621 acquires the subject ID from the processor for an endoscope 20, the acquisition unit 621 may register the subject ID and the endoscope image in association with each other in the examination result DB 631 together with information regarding the examination date and time.

Each of the plurality of learning models 91 is connected in parallel with each other. Therefore, a data flow topology in which the endoscope image output from the acquisition unit 621 is branched and input into each learning model 91 connected in parallel is formed. The plurality of learning models 91 is learning models 91 registered and managed in the learning model management DB 630, and when the same endoscope image is input, the plurality of learning models 91 outputs the same type of diagnosis support information including the presence or absence of a lesion and the like in the endoscope image. The plurality of learning models 91 is learned by, for example, different training data and may output different calculation results (presence or absence of a lesion and the like) even in a case where the same endoscope image is input. Each of the plurality of learning models 91 inputs the endoscope image output from the acquisition unit 621 into the input layer and outputs, to the output unit 622, the diagnosis support information including the presence or absence of a lesion and the like output from the output layer.

The output unit 622 acquires the diagnosis support information output from each of the plurality of learning models 91, refers to the learning model management DB 630, and acquires management information such as a change regarding each learning model 91 that has output the diagnosis support information. The output unit 622 associates the acquired diagnosis support information including the presence or absence of a lesion and the like with the learning model 91 that has output the diagnosis support information, and the output unit 622 further attaches the management information in each learning model 91 to generate screen data for constituting a display screen of the diagnosis support information. The output unit 622 causes the display unit 7 to output the generated screen data for constituting the display screen of the diagnosis support information and causes the display unit 7 to display the display screen of the diagnosis support information. The output unit 622 may output the generated screen data for constituting the display screen of the diagnosis support information to endoscope device 10 and cause the display device 50 connected to the endoscope device 10 to display the display screen.

In the present embodiment, the respective functional parts in a series of processing have been described while being divided into each functional part of the control unit 21 of the processor for an endoscope 20 and each functional part of the control unit 62 of the information processing apparatus 6, but the division of these functional parts is an example and the present invention is not limited thereto. The control unit 21 of the processor for an endoscope 20 may function as all functional parts implemented by the control unit 62 of the information processing apparatus 6, including the learning model 91. That is, the processor for an endoscope 20 may substantially include the information processing apparatus 6. Alternatively, the control unit 21 of the processor for an endoscope 20 may only output the captured image captured by the image sensor, and the control unit 62 of the information processing apparatus 6 may function as all functional parts that perform subsequent processing. Alternatively, the control unit 21 of the processor for an endoscope 20 and the control unit 62 of the information processing apparatus 6 may perform, for example, inter-process communication, thereby functioning in cooperation as respective functional parts in the series of processing.

FIG. 8 is an explanatory diagram illustrating an example of a screen (display screen of diagnosis support information) output to the display unit 7. The information processing apparatus 6 displays the display screen of the diagnosis support information on the display unit 7 on the basis of the screen data for constituting the display screen of the diagnosis support information output from the output unit 622.

The display screen of the diagnosis support information includes an area for displaying information (management information) regarding each learning model 91 and an area for displaying an input endoscope image and diagnosis support information based on the endoscope image.

In the area of the learning model 91, a display field indicating a learning model name, a display field indicating a version, a display field indicating an application date, and a display field indicating a change are arranged. Each of these display fields is generated according to the number of learning models 91 to which the endoscope image is input, and in the present embodiment, each of the display fields is listed using five learning models 91 as an example to constitute the display screen of the diagnosis support information. Contents displayed in each of these display fields are management information regarding each learning model 91 registered in the learning model management DB 630.

In the area of the endoscope image, a display field for displaying the endoscope image and a display field for displaying an output result (diagnosis support information) by each learning model 91 are listed and arranged. The display screen of the diagnosis support information may include information regarding the subject such as the subject ID and the information regarding the examination date and time.

By displaying side by side the output results (diagnosis support information regarding the presence or absence of a lesion and the like) by the plurality of learning models 91 for the same endoscope image, multifaceted diagnosis support information can be provided to the operator of the endoscope 40 such as a doctor. In a case where the plurality of learning models 91 is learned using, for example, training data configured at different time points, a plurality of pieces of diagnosis support information corresponding to time-series changes in each learning model 91 can be provided to the doctor or the like.

By configuring a data flow topology that logically connects the plurality of these learning models 91 in parallel, the endoscope image output from the endoscope device 10 can be branched and efficiently input into each learning model 91. Therefore, as compared with a case where the endoscope image is individually input to each of the plurality of these learning models 91, processing manhours for inputting the endoscope image can be reduced, and even in a case where the number of learning models 91 included in the diagnosis support system S (applied in the diagnosis support system S) is large, it is possible to efficiently cope with the case.

Figure 9:
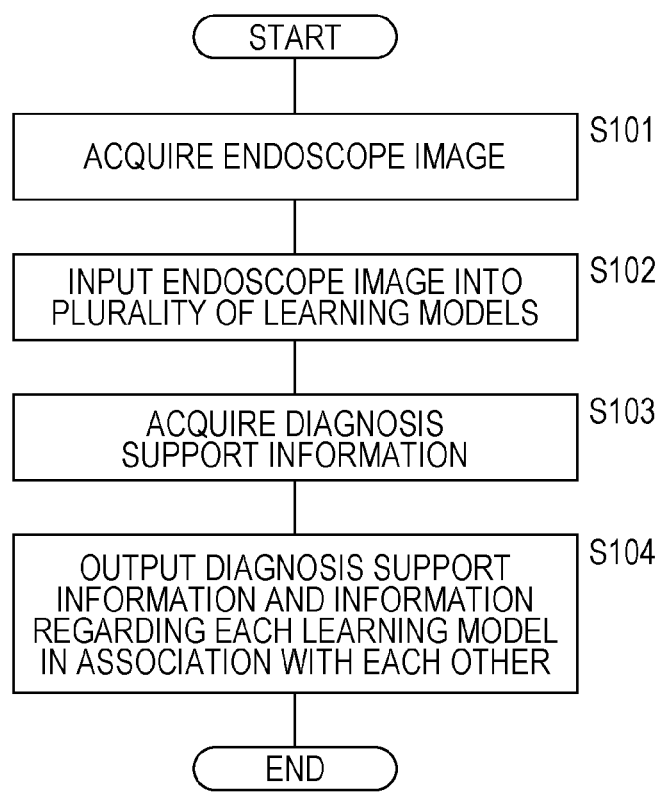
FIG. 9 is a flowchart illustrating an example of a processing procedure performed by the control unit of the information processing apparatus.

FIG. 9 is a flowchart illustrating an example of a processing procedure performed by the control unit 62 of the information processing apparatus 6. For example, the information processing apparatus 6 starts the processing of the flowchart on the basis of contents input from the input unit 8 connected to the information processing apparatus 6.

The control unit 62 of the information processing apparatus 6 acquires an endoscope image output from an endoscope processor (S101). The endoscope image acquired by the control unit 62 from the endoscope processor may be a still image or a video. The control unit 62 may acquire the attribute information of the subject such as the subject ID together with the acquisition of the endoscope image.

The control unit 62 of the information processing apparatus 6 inputs the endoscope image into the plurality of learning models 91 (S102). Each of the plurality of learning models 91 is learned so as to output the same type of diagnosis support information including the presence or absence of a lesion and the like when an endoscope image is input. The control unit 62 inputs the endoscope image acquired from the endoscope processor into each of the plurality of these learning models 91.

The control unit 62 of the information processing apparatus 6 acquires the diagnosis support information regarding the presence or absence of a lesion and the like included in the endoscope image from each of the plurality of learning models 91 (S103). Each of the plurality of learning models 91 to which the endoscope image is input outputs the same type of diagnosis support information including the presence or absence of a lesion and the like. The control unit 62 acquires each piece of the diagnosis support information output from each of the plurality of learning models 91.

The control unit 62 of the information processing apparatus 6 outputs the diagnosis support information and the information regarding each learning model 91 in association with each other (S104). The control unit 62 refers to the learning model management DB 630 stored in the storage unit 63 and acquires the management information such as a version number of each learning model 91. The control unit 62 associates the management information regarding each learning model 91 that has been acquired with reference to the learning model management DB 630 with each piece of the diagnosis support information output from each learning model 91, and the control unit 62 outputs the screen data to form a display screen, for example, in a list format to the display unit 7.

According to the present embodiment, the endoscope image is input into the plurality of learning models 91 that outputs the same type of diagnosis support information, whereby the plurality of pieces of diagnosis support information output from the plurality of learning models 91 is acquired. Therefore, the diagnosis support information for each of the plurality of learning models 91 can be acquired for the same endoscope image. Each piece of the acquired diagnosis support information is output in association with information regarding any learning model 91 that has output the diagnosis support information. Therefore, the operator of the endoscope 40 such as a doctor can easily grasp an influence caused by a change of the learning model by referring to the output result in which the diagnosis support information and the learning model 91 are associated with each other.

According to the present embodiment, the information regarding each of the plurality of learning models 91 includes information regarding a difference between the plurality of learning models 91, for example, a diagnosis threshold, a detection weighting coefficient or training data or the like. Therefore, the operator of the endoscope 40 such as a doctor can easily grasp contents of a change of the learning model 91 and an influence caused by the change on the diagnosis support information by referring to the output result in which the diagnosis support information and the learning model 91 are associated with each other.

According to the present embodiment, at least two learning models 91 among the plurality of learning models 91 are generated by causing neural networks having the same layer configuration to learn using different training data. Therefore, for example, in a case where any of the learning models 91 is relearned, it is possible to efficiently provide, to the doctor or the like, information regarding a difference between diagnosis support information output from the learning model 91 before the relearning and diagnosis support information output from the learning model 91 after the relearning.

In the present embodiment, the control unit 62 of the information processing apparatus 6 inputs the acquired endoscope image into the plurality of learning models 91, acquires the plurality of pieces of diagnosis support information output from each of the plurality of learning models 91, and outputs the acquired plurality of pieces of diagnosis support information and the information regarding each of the plurality of learning models 91 in association with each other, but the present invention is not limited thereto. The control unit 62 of the information processing apparatus 6 may input the acquired endoscope image into a single learning model 91, sequentially execute a plurality of diagnostic logics on the single learning model 91 to acquire a plurality of pieces of output diagnosis support information, uses information regarding each of the plurality of diagnostic logics executed on the learning model 91 as information regarding each of the plurality of learning models 91, and output the acquired plurality of pieces of diagnosis support information and the information regarding each of the plurality of learning models 91 in association with each other. The information regarding each of the plurality of diagnostic logics executed on the learning model 91 has the same meaning as the information regarding each of the plurality of learning models 91, and the control unit 62 of the information processing apparatus 6 may output the information regarding each of the plurality of diagnostic logics executed on the learning model 91 and the acquired plurality of pieces of diagnosis support information in association with each other.

In this case, for the single learning model 91, for example, a network setting state (connection state and setting value of each node) at XX hours, XX minutes, and XX seconds on XX month XX day in a setting 1 before the learning, a network setting state at YY hours, YY minutes, and YY seconds on YY month YY day in a setting 2 immediately after the learning (time point after the setting 1) and a network setting state at ZZ hours, ZZ minutes, and ZZ seconds on ZZ month ZZ day in a setting 3 further after the learning (time point after the setting 2) may be all stored in a predetermined storage area such as the storage unit 63 that can be referred to (accessed) from the learning model 91 (neural network) or may be all stored as data in the learning model 91. Then, the settings 1 to 3 may be switched in time series to output determination results, and each of the determination results may be acquired. On the basis of a plurality of the settings, the plurality of diagnostic logics is executed on the single learning model 91.

In this way, for the single (identical) learning model 91, a plurality of different settings (settings 1 to 3) is made switchable in time series, whereby the determination result based on each of the plurality of diagnostic logics executed in each of the plurality of different settings can be sequentially acquired from the single (identical) learning model 91. Therefore, it is possible to cause one neural network (learning model 91) to work equivalently to a plurality of neural networks (learning models 91) while having less hardware, that is, while reducing an increase in hardware resources such as the processing capability of the control unit 62 or the storage capacity of the storage unit 63.

Second Embodiment

Figure 10:
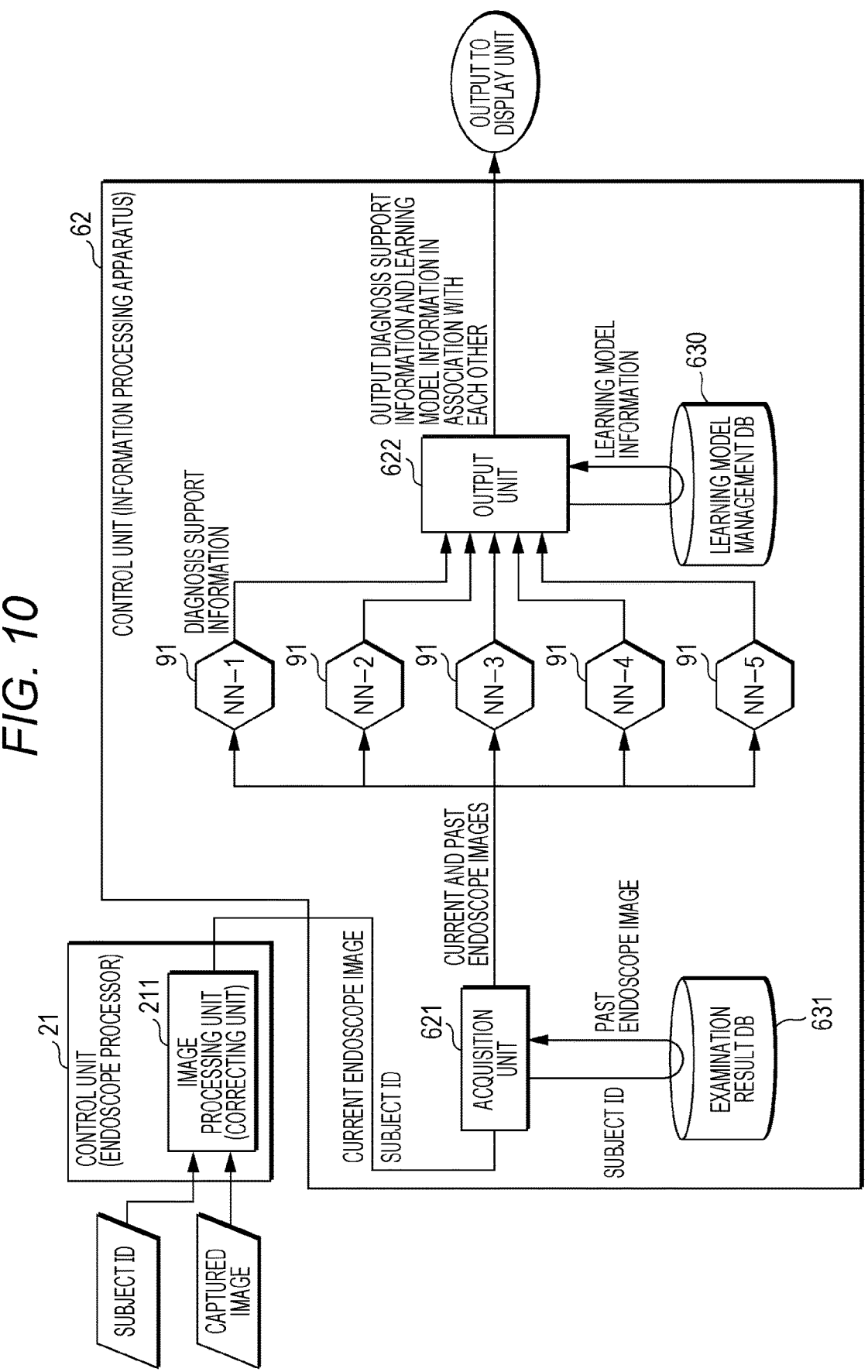
FIG. 10 is a functional block diagram exemplifying functional parts included in a control unit of an information processing apparatus or the like according to a second embodiment (current and past endoscope images).

FIG. 10 is a functional block diagram exemplifying functional parts included in a control unit 62 of an information processing apparatus 6 or the like according to a second embodiment (current and past endoscope images). The information processing apparatus 6 of the second embodiment is different from that of the first embodiment in that a plurality of endoscope images of the same subject captured after a lapse of a predetermined period is input to a plurality of learning models 91.

Similarly to the first embodiment, a control unit 21 of a processor for an endoscope 20 (endoscope device 10) outputs a subject ID input from a keyboard 15 or a touch panel 25 to the information processing apparatus 6 together with an endoscope image.

The acquisition unit 621 acquires the subject ID and the endoscope image output by the processor for an endoscope 20. The acquisition unit 621 uses the acquired subject ID as a search condition (extraction condition) to search (extract) and acquire a past endoscope image based on the subject ID from an examination result DB 631. Similarly to the first embodiment, the acquisition unit 621 inputs, into each of the plurality of learning models 91, the endoscope image (current endoscope image) acquired from the processor for an endoscope 20 and the past endoscope image that is of the same subject as the subject of the current endoscope image and acquired from the examination result DB 631.

Each of the plurality of learning models 91 inputs each of the current and past endoscope images of the same subject output from the acquisition unit 621 to an input layer, and outputs, to an output unit 622, each piece of diagnosis support information regarding the presence or absence of a lesion and the like included in each of the current and past endoscope images output from the output layer.

The output unit 622 acquires the diagnosis support information for each of the current and past endoscope images output from each of the plurality of learning models 91 and acquires management information such as a change regarding each learning model 91 similarly to the first embodiment.

Similarly to the first embodiment, the output unit 622 associates the diagnosis support information with the learning model 91 that has output the diagnosis support information for each of the current and past endoscope images, and the output unit 622 further attaches the management information in each learning model 91 to generate screen data for constituting a display screen of the diagnosis support information. Similarly to the first embodiment, the output unit 622 outputs the screen data to a display unit 7.

FIG. 11 is an explanatory diagram illustrating an example of a screen (result display screen) output to the display unit 7. The information processing apparatus 6 displays the display screen of the diagnosis support information on the display unit 7 on the basis of the screen data for constituting the display screen of the diagnosis support information output from the output unit 622. Similarly to the first embodiment, the display screen of the diagnosis support information includes an area for displaying information (management information) regarding each learning model 91 and an area for displaying an input endoscope image and diagnosis support information based on the endoscope image.

The area of the endoscope image may include, for example, a plurality of rows according to the number of the respective current endoscope images and the number of respective past endoscope images. In the area of the endoscope image, in addition to a display field for displaying the endoscope image, a display field for displaying a date and time when the endoscope image was captured is listed and arranged. In this way, each of the current and past endoscope images and the date and time when the endoscope image was captured are displayed, and each piece of the diagnosis support information output from each of the plurality of learning models 91 for each endoscope image is displayed in a matrix form, whereby the diagnosis support information can be efficiently provided to a doctor or the like.

Diagnosis support information output from the latest learning model 91 can be acquired using the past endoscope image, diagnosis support information output from a past learning model 91 can be acquired using an endoscope image at a current time point, and so-called cross search can be performed using a plurality of endoscope images captured after a lapse of a predetermined period and a plurality of learning models 91 that changes in time series according to an application period. By the cross search, it is possible to efficiently provide, to the doctor or the like, a plurality of pieces of diagnosis support information using each of different endoscope images in time series and each of different learning models 91 in time series.

Figure 12:
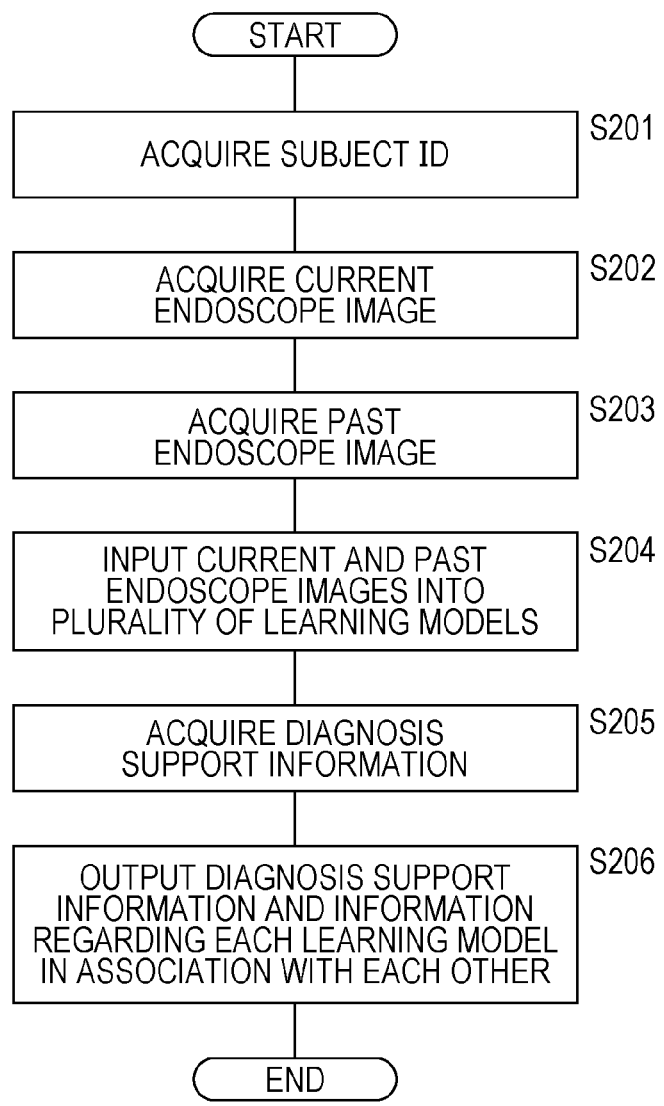
FIG. 12 is a flowchart illustrating an example of a processing procedure performed by the control unit of the information processing apparatus.

FIG. 12 is a flowchart illustrating an example of a processing procedure performed by the control unit 62 of the information processing apparatus 6. For example, the information processing apparatus 6 starts the processing of the flowchart on the basis of contents input from the input unit 8 connected to the information processing apparatus 6.

The control unit 62 of an endoscope processor acquires the subject ID (S201). The control unit 62 acquires the subject ID output from the endoscope processor.

The control unit 62 of the endoscope processor acquires the endoscope image (corresponding to the current endoscope image) (S202). Similarly to the first embodiment, the control unit 62 acquires the endoscope image (corresponding to the current endoscope image) output from the endoscope processor. The control unit 62 may register the acquired subject ID and the current endoscope image in the examination result DB 631 in association with each other.

The control unit 62 of the endoscope processor acquires the past endoscope image (S203). The control unit 62 acquires the past endoscope image corresponding to the subject ID from the examination result DB 631 on the basis of the acquired subject ID.

The control unit 62 of the endoscope processor inputs the current and past endoscope images to the plurality of learning models 91 (S204). Similarly to the first embodiment, the control unit 62 inputs the acquired current and past endoscope images to each of the plurality of learning models 91.

The control unit 62 of the endoscope processor acquires the diagnosis support information (S205). The control unit 62 acquires each piece of the diagnosis support information based on the current and past endoscope images output from each of the plurality of learning models 91.

The control unit 62 of the endoscope processor outputs the diagnosis support information and the information regarding each learning model 91 in association with each other (S206). Similarly to the first embodiment, the control unit 62 associates the management information regarding each learning model 91 acquired from the learning model management DB 630 with each piece of the diagnosis support information for the current and past endoscope images output from each learning model 91 and outputs the screen data to form a display screen, for example, in a matrix format to the display unit 7.

According to the present embodiment, since the endoscope image includes a plurality of endoscope images of the same subject captured after a lapse of a predetermined period, the diagnosis support information by the plurality of learning models 91 for the plurality of these endoscope images can be acquired. Therefore, for example, the endoscope image captured in the past can be input into the latest learning model included in the plurality of learning models 91, and more appropriate diagnosis support information can be provided to the doctor or the like.

Third Embodiment

Figure 13:
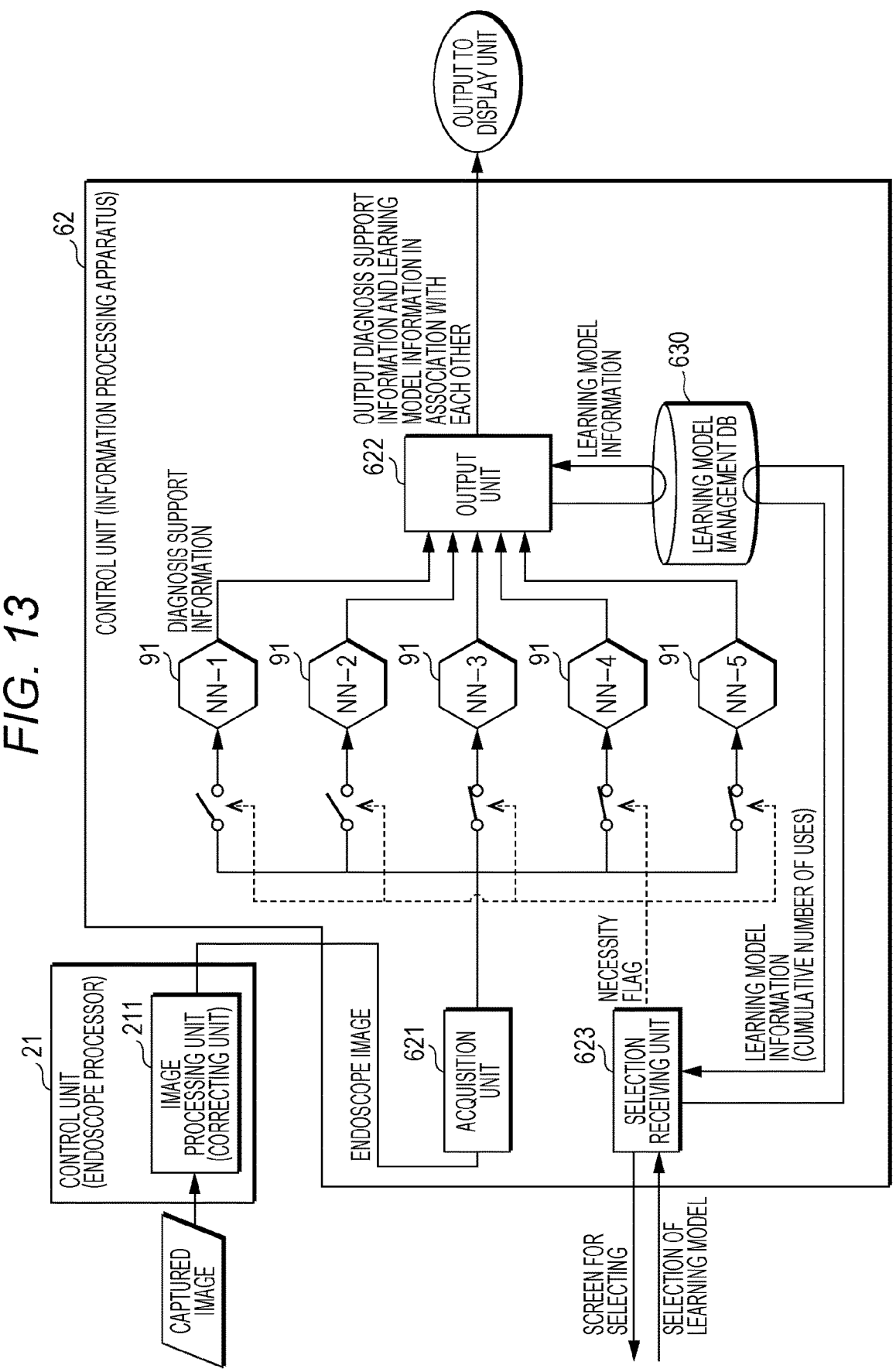
FIG. 13 is a functional block diagram exemplifying functional parts included in a control unit of an information processing apparatus or the like according to a third embodiment (selection of a learning model).

FIG. 13 is a functional block diagram exemplifying functional parts included in a control unit 62 of an information processing apparatus 6 or the like according to a third embodiment (selection of a learning model 91). The information processing apparatus 6 of the third embodiment is different from that of the first embodiment in that an operation of selecting a learning model 91 to be used to acquire diagnosis support information is received.

The control unit 62 of the information processing apparatus 6 executes a program P stored in a storage unit 63, thereby functioning as an acquisition unit 621 and an output unit 622 similarly to the first embodiment and further functioning as a selection receiving unit 623.

The selection receiving unit 623 refers to a learning model management DB 630 stored in the storage unit 63 and acquires management information such as a version number of each learning model 91. The selection receiving unit 623 generates screen data constituting a screen for selecting that is for receiving a selection of a learning model 91 to be used (screen for selecting a learning model 91 to be used) on the basis of the acquired management information regarding each learning model 91 and outputs the screen data to a display unit 7. The selection receiving unit 623 receives the selection of a learning model 91 by a doctor or the like on the screen for selecting, generates, for example, flag information (necessity flag) for distinguishing the selected learning model 91, and sets only the selected learning model 91 to be valid in a plurality of learning models 91 applied in a diagnosis support system S.

Similarly to the first embodiment, the acquisition unit 621 acquires an endoscope image output by a processor for an endoscope 20 and outputs the acquired endoscope image to each selected learning model 91. Similarly to the first embodiment, each selected learning model 91 acquires the endoscope image and outputs diagnosis support information. Alternatively, the acquisition unit 621 may output the endoscope image to all of the plurality of learning models 91, and only the selected learning model 91 (valid learning model 91) may acquire the endoscope image and output the diagnosis support information on the basis of the setting by the selection receiving unit 623.

Similarly to the first embodiment, the output unit 622 acquires the diagnosis support information output from each selected learning model 91, acquires the management information regarding each learning model 91 selected from the learning model management DB 630, generates screen data for constituting a display screen of the diagnosis support information, and outputs the screen data to the display unit 7.

FIG. 14 is an explanatory diagram illustrating an example of a screen (screen for selecting a learning model 91) output to the display unit 7. The information processing apparatus 6 displays the screen for selecting a learning model 91 to be used on the display unit 7 on the basis of the screen data for constituting the screen for selecting a learning model 91 to be used output from the selection receiving unit 623.

The screen for selecting a learning model 91 to be used includes a display field indicating a learning model name, a display field indicating a version, a display field indicating an application date, a display field indicating a change, a display field indicating the cumulative number of uses, and an input field for receiving the input of a selection operation as to whether to use a learning model 91.

Each of these display fields is generated according to the number of learning models 91 to which the endoscope image is input, and in the present embodiment, each of the display fields is listed using five learning models 91 as an example to constitute the screen for selecting a learning model 91 to be used. Contents displayed in each of these display fields are management information regarding each learning model 91 registered in the learning model management DB 630.

On the basis of the contents displayed in each of the display fields, the doctor or the like can grasp the history of each learning model 91 desired to be used and can grasp the use records or popularity of each learning model 91 by referring to the cumulative number of uses. Therefore, information for selecting an appropriate learning model 91 according to the type of diagnosis or a subject can be efficiently provided to the doctor or the like.

The input field for the selection operation includes an operation input unit that receives the input of the selection operation using, for example, a toggle switch, a radio button, a pull-down menu, or the like, and a learning model 91 to be used is selected (specified) according to contents input into the operation input unit. In the present embodiment, as an example, the operation input unit includes a toggle switch, and three learning models 91 (NN-2, NN-3, and NN-5) are selected among the plurality of learning models 91.

Contents (selection of a plurality of learning models 91) input on the screen for selecting a learning model 91 to be used by the doctor or the like are received by the selection receiving unit 623, and as described above, the selected learning models 91 are set to be valid.

To use the plurality of learning models 91 applied in the diagnosis support system S, information regarding the application date and history such as a change and the cumulative number of uses of each learning model 91 is provided to the doctor or the like, whereby it is possible to support the selection of the learning models 91 by the doctor or the like. By displaying the diagnosis support information output by the selected learning models 91, the diagnosis support information can be efficiently provided to the doctor or the like.

FIG. 15 is a flowchart illustrating an example of a processing procedure performed by the control unit 62 of the information processing apparatus 6. For example, the information processing apparatus 6 starts the processing of the flowchart on the basis of contents input from the input unit 8 connected to the information processing apparatus 6.

The control unit 62 of an endoscope processor acquires information regarding the learning model 91 (S301). The control unit 62 acquires the management information such as the version number of each learning model 91 from the learning model management DB 630.

The control unit 62 of the endoscope processor displays the screen for selecting a learning model 91 (S302). The control unit 62 generates screen data constituting the screen for selecting a learning model 91 to be used on the basis of the acquired management information regarding each learning model 91 and displays the screen for selecting on the display unit 7.

The control unit 62 of the endoscope processor receives the selection of the learning models 91 (S303). The control unit 62 receives the selection of the learning models 91 on the basis of the contents input on the screen for selecting a learning model 91 to be used.

The control unit 62 of the endoscope processor acquires the endoscope image (S304). Similarly to the first embodiment, the control unit 62 acquires the endoscope image. Similarly to the second embodiment, the control unit 62 may acquire each of current and past endoscope images.

The control unit 62 of the endoscope processor inputs the endoscope image into the selected learning models 91 among the plurality of learning models 91 (S305). The control unit 62 inputs the acquired endoscope image into the selected learning models 91 among the plurality of learning models 91.

The control unit 62 of the endoscope processor acquires the diagnosis support information (S306). The control unit 62 acquires the diagnosis support information output by the selected learning models 91.

The control unit 62 of the endoscope processor outputs the diagnosis support information and information regarding each selected learning model 91 in association with each other (S307). Similarly to the first embodiment, the control unit 62 associates the diagnosis support information with the information regarding each selected learning model 91 and outputs the screen data to form a display screen, for example, in a list format to the display unit 7. In a case where the control unit 62 acquires the current and past endoscope images similarly to the second embodiment, the control unit 62 outputs in association with each piece of the diagnosis support information for the current and past endoscope images output from each selected learning model 91 and outputs the screen data to form a display screen, for example, in a matrix to the display unit 7.

According to the present embodiment, since an operation of selecting any learning model 91 among the plurality of learning models 91 is received, the doctor or the like can select a single or a plurality of learning models 91 required to be used for acquiring the diagnosis support information. Since the diagnosis support information output from the selected learning model 91 and the information regarding the selected learning model 91 are output in association with each other, the diagnosis support information output by the learning model 91 based on the selection by the doctor or the like can be efficiently provided to the doctor or the like.

According to the present embodiment, to receive the operation of selecting any learning model 91 among the plurality of learning models 91, information regarding the cumulative number of uses of each of the plurality of learning models 91 is displayed. Therefore, the information regarding the cumulative number of uses of each of the learning models 91 can be provided to the doctor or the like who selects a learning model 91, and information for supporting a determination as to which learning model 91 is to be used can be efficiently provided to the doctor or the like.

The embodiments disclosed this time should be considered to be exemplary in all respects and not to be restrictive. The technical features described in the respective embodiments can be combined with each other, and the scope of the present invention is intended to include all modifications within the scope of the claims and the scope equivalent to the claims.

REFERENCE SIGNS LIST

S diagnosis support system
10 endoscope device
15 keyboard
16 storage shelf
20 processor for an endoscope
21 control unit
211 image processing unit
22 main storage device 23 auxiliary storage device
24 communication unit
25 touch panel
26 display device I/F
27 input device I/F
28 reading unit
31 connector for an endoscope
311 electrical connector
312 optical connector
33 light source
34 pump
35 water supply tank
36 air supply/water supply metal port
40 endoscope
43 operation unit
431 control button
433 bending knob
44 insertion portion
441 soft portion
442 bending section
443 distal tip
45 bend preventing portion
48 scope connector
49 universal cord
50 display device
6 information processing apparatus
61 communication unit
62 control unit
621 acquisition unit
622 output unit
623 selection receiving unit
63 storage unit
630 learning model management DB
631 examination result DB
632 recording medium
P program
64 input/output I/F
7 display unit
8 input unit
91 learning model

The invention claimed is:

1. A non-transitory computer-readable storage medium containing a program for causing a computer to execute processing comprising:
acquiring an endoscope image captured by an endoscope including
an inserter having
a distal tip with an image sensor,
a bending section, and
a proximal section, the bending section being positioned between the distal tip and the proximal section;
a bend-preventer having a first end connected to the proximal section of the inserter, and a second end;
an operator having a first end connected to the second end of the bend-preventer, and a bender connected to the bending section of the inserter and configured to actuate bending of the bending section;
a processor; and
a cord one having one end connected to the operator and another end connected to the processor;
inputting, with the processor, the acquired endoscope image into a plurality of learning models learned so as to output diagnosis support information regarding a lesion included in the endoscope image;
acquiring, with the processor, a plurality of pieces of diagnosis support information output from each of the plurality of learning models; and
outputting, with the processor, a plurality of pieces of the acquired diagnosis support information and information regarding each of the plurality of learning models in association with each other, wherein
at least two learning models among the plurality of learning models include neural networks having the same layer configuration, and
each piece of training data for learning the two learning models is different.

2. The non-transitory computer-readable storage medium containing a program according to claim 1, wherein
the information regarding each of the plurality of learning models includes information regarding a difference between the plurality of learning models.

3. The non-transitory computer-readable storage medium containing a program according to claim 1, wherein
the endoscope image includes a plurality of endoscope images captured by the endoscope after a lapse of a predetermined period,
each of the plurality of endoscope images is input into each of the plurality of learning models,
a plurality of pieces of diagnosis support information for each of the plurality of endoscope images output from each of the plurality of learning models is acquired, and
a plurality of pieces of the acquired diagnosis support information and information regarding time points at which the plurality of endoscope images was captured are output in association with each other.

4. The non-transitory computer-readable storage medium containing a program according to claim 1, wherein
an operation of selecting any learning model among the plurality of learning models is received,
diagnosis support information output from the selected learning model is acquired, and
the acquired diagnosis support information and information regarding the selected learning model are output in association with each other.

5. The non-transitory computer-readable storage medium containing a program according to claim 4, wherein
information regarding the cumulative number of uses of each of the plurality of learning models is displayed.

6. The non-transitory computer-readable storage medium containing a program according to claim 1, wherein
diagnosis support information regarding a lesion included in the endoscope image output from each of the plurality of learning models is the same type of information including at least one of the presence or absence of a lesion, the type of symptom of the lesion, a stage of symptom of the lesion, and a location of the lesion included in the endoscope image.

7. An information processing method for causing a computer to execute processing comprising:
providing an endoscope including
an inserter having
a distal tip with an image sensor,
a bending section, and
a proximal section, the bending section being positioned between the distal tip and the proximal section;
a bend-preventer having a first end connected to the proximal section of the inserter, and a second end;
an operator having a first end connected to the second end of the bend-preventer, and a bender connected to the bending section of the inserter and configured to actuate bending of the bending section;
a processor; and
a cord one having one end connected to the operator and another end connected to the processor;
acquiring, with the processor, an endoscope image captured by an endoscope;
inputting, with the processor, the acquired endoscope image into a plurality of learning models learned so as to output diagnosis support information regarding a lesion included in the endoscope image;
acquiring, with the processor, a plurality of pieces of diagnosis support information output from each of the plurality of learning models; and
outputting, with the processor, a plurality of pieces of the acquired diagnosis support information and information regarding each of the plurality of learning models in association with each other, wherein
at least two learning models among the plurality of learning models include neural networks having the same layer configuration, and
each piece of training data for learning the two learning models is different.

8. An information processing apparatus comprising:
an inserter having
   a distal tip with an image sensor,
   a bending section, and
   a proximal section, the bending section being positioned between the distal tip and the proximal section;
a bend-preventer having a first end connected to the proximal section of the inserter, and a second end;
an operator having a first end connected to the second end of the bend-preventer, and a bender connected to the bending section of the inserter and configured to actuate bending of the bending section;
a processor; and
a cord one having one end connected to the operator and another end connected to the processor,
wherein the processor is configured to
   acquire an endoscope image captured by the image sensor,
   input the acquired endoscope image into a plurality of learning models learned so as to output diagnosis support information regarding a lesion included in the endoscope image, and
   acquire a plurality of pieces of diagnosis support information output from each of the plurality of learning models, and output a plurality of pieces of the acquired diagnosis support information and information regarding each of the plurality of learning models in association with each other, wherein
at least two learning models among the plurality of learning models include neural networks having the same layer configuration, and
each piece of training data for learning the two learning models is different.

\* \* \* \* \*